United States Patent

Van Der Heiden et al.

[11] Patent Number: 5,368,586
[45] Date of Patent: Nov. 29, 1994

[54] CLOSURE FOR A DRUG-VIAL

[75] Inventors: Johannes Van Der Heiden, Groningen; Herbertus E. Hilbrink, Emmen, both of Netherlands

[73] Assignee: NPBI Nederlands Produktielaboratorium voor Bloedtransfusieapparatuur en Infusievloeistoffen B.V., Emmer-Compascuum, Netherlands

[21] Appl. No.: 816,494

[22] Filed: Dec. 27, 1991

Related U.S. Application Data

[63] Continuation-in-part of Ser. No. 719,728, Jun. 21, 1991, Pat. No. 5,224,937.

[51] Int. Cl.⁵ .............................................. A61M 5/00
[52] U.S. Cl. ................................... 604/403; 604/416; 604/408
[58] Field of Search ............... 604/405, 406, 413, 415, 604/416, 905, 200; 215/DIG. 3, 249-251

[56]  References Cited

U.S. PATENT DOCUMENTS

| | | | |
|---|---|---|---|
| 3,484,849 | 12/1969 | Huebner et al. | 604/413 |
| 3,941,171 | 3/1976 | Ogle | 141/309 |
| 4,013,860 | 3/1977 | Hosterman . | |
| 4,157,723 | 6/1979 | Granzow . | |
| 4,186,292 | 1/1980 | Acker . | |
| 4,234,095 | 11/1980 | Safianoff | 215/232 |
| 4,369,799 | 1/1983 | Napoleon . | |
| 4,390,832 | 6/1983 | Taylor . | |
| 4,607,671 | 8/1986 | Aalto et al. | 141/329 |
| 4,611,643 | 9/1986 | Beebe . | |
| 4,614,267 | 9/1986 | Larkin . | |
| 4,619,642 | 10/1986 | Spencer . | |
| 4,737,214 | 4/1988 | Leurink . | |
| 4,759,756 | 7/1988 | Forman . | |
| 4,892,710 | 1/1990 | Wong et al. | 604/403 X |
| 4,944,736 | 7/1990 | Holtz | 604/423 |
| 4,997,429 | 3/1991 | Dickerhoff et al. | 504/411 |
| 4,997,430 | 5/1991 | Van Der Heiden . | |
| 5,114,030 | 5/1992 | Conard | 215/249 |
| 5,125,415 | 6/1992 | Bell | 128/766 |
| 5,125,522 | 6/1992 | Pezzoli et al. | 215/250 |
| 5,224,937 | 7/1993 | Van Der Heiden et al. | 604/200 |

*Primary Examiner*—Sam Rimell
*Attorney, Agent, or Firm*—Herbert Dubno; Andrew Wilford

[57] ABSTRACT

A closure assembly for a vial for a sterile drug comprises a body fitted with a sealable tube that has a seal that hermetically closes it on one end and that is in communication with the inside of the drug vial on the other end. The sterile drug can be reconstituted and/or diluted in an IV solution by means of sterile docking in a closed system. Via the tube on this closure assembly, the vial is connected to a component with a closed sealable tube, such as an IV solution container or a syringe by unsealing and joining the outer ends of the tubes to each other in a sterile docking procedure. If the drug needs reconstitution or dilution, a sterile fluid can first be introduced into the drug vial from the flexible container or from the syringe via the joined ends of the tubes. When the drug is dissolved, the solution can be aspirated to the flexible container or to the syringe. Subsequently, the tube connecting the vial and the component can be sealed and the seal can be cut.

20 Claims, 4 Drawing Sheets

CLOSURE FOR A DRUG-VIAL

This application is a continuation in part of U.S. application Ser. No. 07/719,728, filed Jun. 21, 1991 now U.S. Pat. No. 5,224,937.

FIELD OF THE INVENTION

My present application relates to a closure for a drug vial, to a method of preparing a sterile solution, e.g. for IV administration, and to a medicament package.

BACKGROUND OF THE INVENTION

Many injectable drugs are supplied in a vial with a rubber closure and an aluminum cap. The drugs may either be supplied in the powdered form or they may be supplied in a solution in the liquid form. Many of these drugs require reconstitution and/or dilution in an IV (intravenous) solution before they can be administered to the patient. Generally, these are highly potent pharmacological agents that must be injected directly into a vein to get the desired effect.

These injectable drug products derive from many different suppliers. Therefore, a variety of injectable products exist with different vials, closures and caps. However, some standards have been generally accepted. The closures, as well as the vials and the caps of these injectable drug products are standardized by ISO. ISO sets standard for dimensions and for physical, chemical and biological properties. Together, these standards can form a guarantee for a good leaktight fit of the vial, the closure and the cap, and thus for the sterility of the drug product upon storage. The closure generally is formed by a body that has a membrane and that has a ring that fits in the mouth of the drug vial. These closures are generally made from rubber. Rubber is elastomeric and can therefore be compressed between the mouth of the container and the aluminum cap, thus forming the required hermetically closed packaging needed for injectable products. Secondly, rubber is self-sealing and can easily be pierced, thus allowing for the aseptic introduction of diluent and withdrawal of the contents of the vial by means of a needle and a syringe at the time of use.

The most common intravenous solutions that are used for the reconstitution or dilution of drugs are 5% dextrose and 0.9% sodium chloride solutions, the latter generally being referred to as physiological saline. These intravenous solutions may be packaged in rigid containers such as glass bottles, in semi-rigid containers made of a plastic, e.g. polypropylene, or in flexible containers made of e.g. PVC.

The diluted and/or reconstituted drug solution - after it is taken from the drug vial- may be administered to the patient from one of these containers in which the solution is supplied, or from a syringe. Several pumps and controllers are available for the slow administration of these drug solutions from one of these large-volume containers. From a syringe, the solution may be injected fast as an IV bolus, or slowly over a period of time with the aid of a syringe pump.

The state of the art in preparing a powdered drug in an intravenous form is to first inject a portion of the diluent into the drug vial. This step is often referred to as a reconstitution. The diluent for this reconstitution may be taken from the IV container in which the final dilution will take place or may be taken from a different IV container or from an ampoule. First, the syringe is filled with the diluent. Then the needle of the syringe is pierced through the rubber stopper of the drug vial and the diluent is introduced into the vial by the syringe. After mixing and dissolution of the powder in the vial, the solution is drawn back into the syringe and may be injected from the syringe into the intravenous container from which it will be administered or it may be injected directly into the patient's vein from the syringe. If the drug in the vial is already in a dissolved form, it can be taken directly from the vial by the syringe.

If an admixture is prepared in an IV solution, after reconstitution and/or dilution, the container is inspected for particulate matter and leakage. If the container leaks, it will be discarded. After labelling and packaging, it is transported. After inspection and after introduction into an administration set, the reconstituted solution is administered to the patient.

Many problems are associated with the reconstitution and/or dilution of drugs in this way. They derive mainly from the fact that the transfer of material during reconstitution and dilution takes place in an essentially open system. Therefore, many precautions have to be taken to prevent foreign material from entering the solution and to prevent the drug solution from contaminating the environment. Micro-organisms that are introduced into the IV solution during reconstitution or dilution may induce fever and sepsis in the patient. Particulate matter that is inadvertently introduced into the solution may block the patient's arteries or veins.

Therefore, many precautions are taken to prevent foreign material from entering the solution.

However, the product itself may also pose a hazard for the medical staff. This hazard derives mainly from the fact that some of the commonly prepared drugs are extremely toxic, even in low doses if exposure takes place over a period of time. This is especially true for the cytotoxic drugs that are used to treat cancer. Most of these are themselves carcinogenic. The main risks of exposure to these drugs is associated with the use of needles in essentially open systems. For that reason, several precautions have been implemented in the hospitals to prevent inadvertent exposure of personnel to these drugs. Of special concern are spillage, leakage and the formation of aerosols.

These dangers may occur during reconstitution, during transport to the ward, during administration to the patient and through waste. During the process of reconstitution of the drug, of special concern is the withdrawal and addition of the drug solution from and to the drug and IV containers. The needle cuts through membranes of these containers. Upon removal of this needle from these containers, there is generally some leakage from small capillaries which remain in the membrane at the place where the needle has cut through the closure. These capillaries usually contain some fluid which may include the drug solution. If the pressure in the container is increased, this may lead to the ejection of aerosols. Also, the ruptured membrane with the cut rubber will remain on the IV container and may therefore not only give rise to leakage during reconstitution, but can also leak during transport or during administration of the drug.

Other disadvantages of this method of reconstitution of a drug in an infusion solution include the risk of accidental puncture of a flexible container and the risk of interaction between the drug solution and the rubber closure. Also, coring or laceration of the rubber membrane can take place when it is punctured with a needle.

This may lead to rubber particles in the solution. Generally, this method of reconstitution which makes use of a needle, is tiresome for the medical practitioner.

For these reasons, reconstitution or dilution of drugs is generally only performed under supervision of the hospital pharmacy by skilled personnel following strict procedures, thoroughly disinfecting all materials that are used, wearing protective clothing and working in a separate area in a LAF-cabinet.

To prevent inadvertent exposure to cytotoxic drugs, most hospitals follow even more stringent procedures which are based on guidelines issued by e.g. the American Society of Hospital Pharmacists, or which are based on local rules or regulations. Generally, they comprise working in a special (down-flow) LAF-cabinet, wearing special protective clothing and safety goggles and special rules for handling of the product and of the waste that is generated during reconstitution.

Because reconstitution takes place in an aseptic way, the shelf life of the products is very limited, to prevent the massive outgrowth of accidental bacterial contamination. Depending upon the nature of the product, the storage conditions and the policy of the hospital, the stability period for the reconstituted product is limited to 1 day to 7 days. However, patient medication is frequently changed. Due to the limited expiry after aseptic preparation, the product usually cannot be used for the treatment of another patient. Therefore, reconstitution under aseptic conditions generates a considerable amount of drug products that must be discarded.

Several systems have been developed to improve the reconstitution process of drugs for an IV solution. Generally, these systems allow for easier and faster reconstitution and/or dilution. For example, several types of double-pointed needles, commonly referred to as transfer needles, have been developed. A needle of this type, and the reconstitution process with this needle, are described in U.S. Pat. No. 4,759,756.

In U.S. Pat. No. 4,614,267, a dedicated system is described in which a dedicated vial containing a drug, can be screwed into a container with the IV solution.

In U.S. Pat. No. 4,997,430, an apparatus and connector are described for direct coupling of a medicament in a drug vial to an IV solution in a container.

In WO 89/00836 a closure for a drug vial is disclosed that is fitted with a connector to which a syringe can be coupled directly. Also, a special penetrating unit for a closure is disclosed.

None of these systems, however, is truly a closed system; all require at least one aseptic step in the reconstitution or dilution process. Therefore, these systems still require special procedures and still have many of the above-mentioned disadvantages.

Several techniques have been described that are, as such, capable of opening fluid communication in a closed system. These techniques are often referred to as sterile docking. Such techniques may employ special connectors that can be welded in a sterile manner as described in U.S. Pat. Nos. 4,157,723 and 4,611,643.

Most of these sterile docking techniques, however, make use of a simple piece of sealable tubing that is closed on one end and is in communication with a component on the other end. This tubing may be of a material such as PVC (polyvinylchloride). The components that need to be coupled must both be fitted with such a piece of tubing. These tubes are put in an apparatus for sterile docking and are docked, that is unsealed, connected and subsequently sealed together. Such systems are described in U.S. Pat. Nos. 4,369,799, 4,619,642, and 4,737,214.

Such an apparatus for making sterile connections is marketed in the U.S. by the Haemonetics company. In addition a system to use sterile docking to connect a bag containing a sterile CAPD fluid to the intraperitoneal catheter of a patient is marketed in Europe by the Gambro company. Finally, sterile docking is used in some blood banks for the production of blood components. For this purpose, sterile fluids in flexible containers with a PVC tube for sterile docking are marketed in the Netherlands by NPBI.

OBJECTS OF THE INVENTION

It is an object of the present invention to provide an improved closure assembly for injectable products whereby earlier drawbacks are avoided.

Another object is to provide an assembly which allows for an improved method and packaging for the reconstitution and/or dilution of injection products in which many of the drawbacks of the methods of reconstitution in open systems as mentioned above, are obviated.

More specifically, an object of the present invention is to allow for the use of a closed system (sterile docking) for the reconstitution and/or dilution of these drugs.

SUMMARY OF THE INVENTION

These objects are attained in accordance with the instant invention which comprises a closure assembly for a sterile drug product having a body that can fit hermetically over the mouth of a drug vial and that has attached a closed, sealable tube the inside of which is in communication with the inside of the vial and sealed at its opposite end.

The closure assembly is placed on a drug container by a drug manufacturer after filling of the drug in the vial. Subsequently the product may be sterilized and/or lyophilized by the manufacturer.

This drug product, fitted with a closed sealable tube, is used in conjunction with a flexible IV container with a closed sealable tube or with a syringe with a closed sealable tube.

The method comprises the steps of first unsealing and joining the outer ends of the tubes to each other in a sterile docking procedure. In this procedure, no foreign material such as micro-organisms is introduced. Also, no drug or drug solution is spilled into the environment.

If the drug needs reconstitution or dilution, a sterile fluid can first be introduced into the drug vial from the flexible container or from the syringe via the joined ends of the tubes. When the drug is dissolved, the solution can be aspirated through the unsealed and joined ends, thus transferring the medicament from its original vial to the IV solution container or to the syringe.

Subsequently, the tube can be sealed and the seal can be cut to form two new seals on the tube outer ends.

The closure assembly can be fitted with an adaptor mounted on said body and receiving said vial with a tight fit. It is also within the scope of this invention to provide a filter and/or a break-away connector in the tube intermediate the ends thereof and/or a clamp on the tube intermediate the ends thereof actuatable to restrict flow through the tube.

BRIEF DESCRIPTION OF THE DRAWING

The above and other objects, features and advantages of the invention will become more readily apparent from the following description, reference being made to the accompanying drawing in which.

SPECIFIC DESCRIPTION

Figure 1:
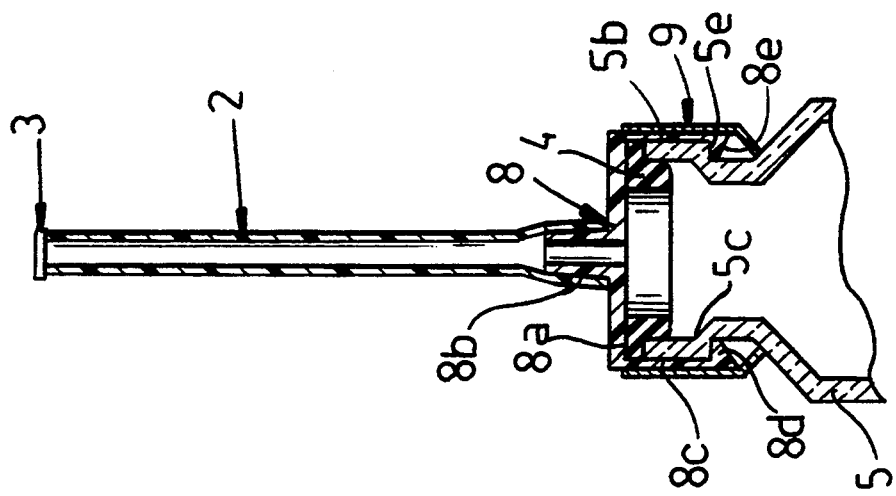
FIGS. 1 to 3 are cross sectional views of a closure assembly according to the present invention, mounted on a drug vial.

FIG. 1 shows a closure according to the present invention. The body 1 of this closure is fitted with a sealable tube 2 having an outer end provided with a seal 3 that hermetically closes it. The tube can be attached to this body by means of gluing, welding or clamping. The body is fitted with a ring 4 that can form a hermetically closed seal with a standard drug vial. For that purpose, the critical sizes of the closure will generally conform to ISO standards to guarantee a leaktight fit with the mouth of a standard bottle according to ISO. The ring that must guarantee a leaktight fit is made of a natural elastomer like rubber or a synthetic elastomer. If the ring is made of an elastomeric material, the body of the closure may be made of any material such as PVC, polyethylene, polycarbonate etc.

This closure can be secured to the drug vial with a cap 6.

The cap 6 may have an upper flange 6a overlying the disk-shaped portion 1a of the body 1 which is formed unitarily with a tubular formation 1b over which the tube 2 is forced and to which the tube is permanently affixed in the manner previously described, e.g. by heat sealing, the use of an adhesive or the like. The sealing ring 4 is likewise formed with a flange 4a which overlies the upper edge 5a of the mouth of the vial 5 and is flush with the outer surface 5b of the mouth 5c thereof. The mouth 5c of the vial is set outwardly of the neck 5d thereof so that another flange 6b of the cap 6 can underlie a shoulder 5e formed by the mouth. A cylindrical wall unitary with the flange 6a and 6b of the cap 6, interconnects these flanges.

Figure 2:
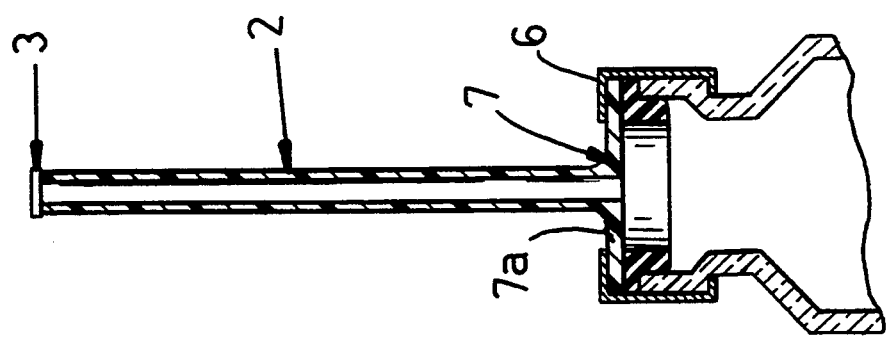

FIG. 2 shows the closure in which the tube is integrated with the body and thus forms an integral part 7 of the closure. In that case the body is made of a sealable material such as PVC or a polyolefin such as polyethylene or polypropylene.

The cap 6 of FIG. 2 is identical to that of FIG. 1, although the body 7, which is here unitary with the tube 2, is formed by a disk 7a from which the tube 2 extends directly in place of the stub 1b of the previous embodiment.

Figure 3:
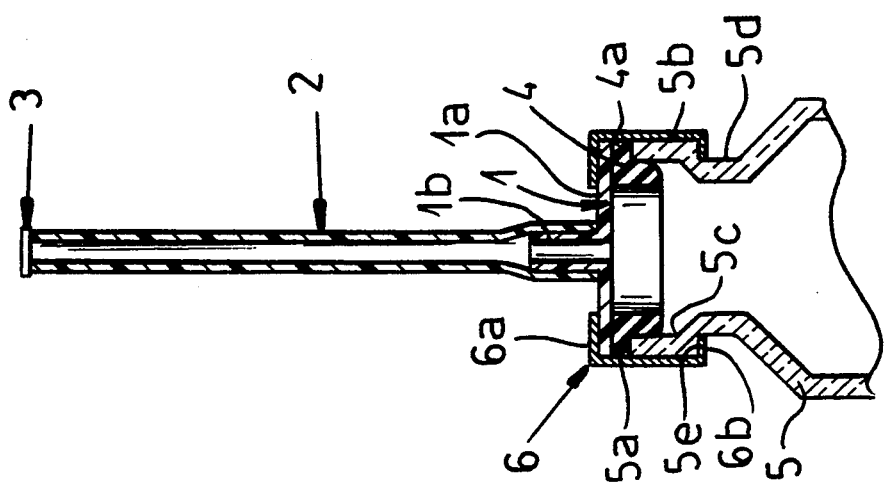

FIG. 3 shows the body of the closure fitted with an adaptor 8 which serves as a cap. This click- or snap-connector fits tightly over the mouth of a drug vial, thus securing the closure to the vial. In this embodiment, a separate cap is not necessary as the closure and the cap are integrated. The connection between the vial and this adapter may be equipped with a tamper evidence 9 for reasons of proof of sterility. The cap can be made of a (semi-)rigid plastic material such as polycarbonate.

While the cap 6 in the embodiments of FIGS. 1 and 2 serves to retain the body on the sealing ring which is in turn provided upon the mouth of the vial, in the embodiments of FIGS. 3–7, 8A–8D and 9, the disk 8a of the body, which can have a stub 8b onto which the tube 2 is permanently mounted, can be formed with an apron 8c extending around the cylindrical wall 5b of the mouth 5c of the vial 5 and can have a barb 8d extending inwardly to forceably engage the shoulder 5e on the underside of this mouth. To enable the body 8 to be forced over the sealing ring 4 and the mouth 5c of the vial, the outer edge 8e of the barb can be bevelled. This, of course, ensures a snap fit between the body 8 and the mouth, retaining the ring 4 under compression.

Figure 4:
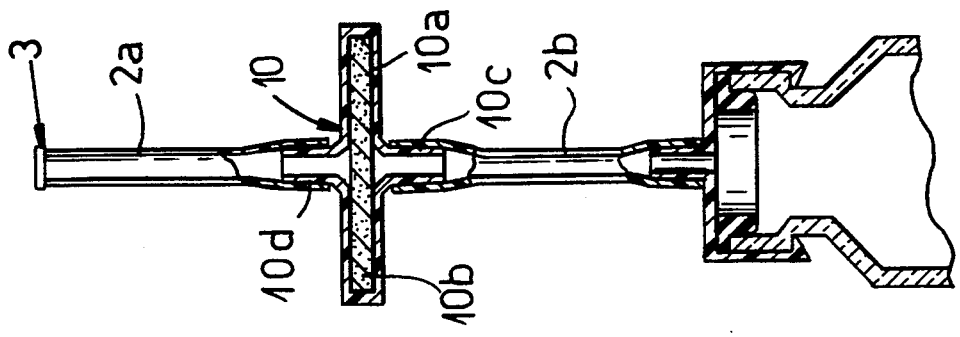

FIG. 4 shows the tube fitted with a filter 10. The filter is intended for the removal of particulate matter and/or undissolved drug particles from the solution. The pore size of the filter may range from 200 $\mu$m to 0.2 $\mu$m, and is preferably around 5 $\mu$m.

The filter 10 comprises a housing 10a for a filter disk 10b, the housing having stubs 10c and 10d over which are fitted the tube segments 2a and 2b.

Figure 5:
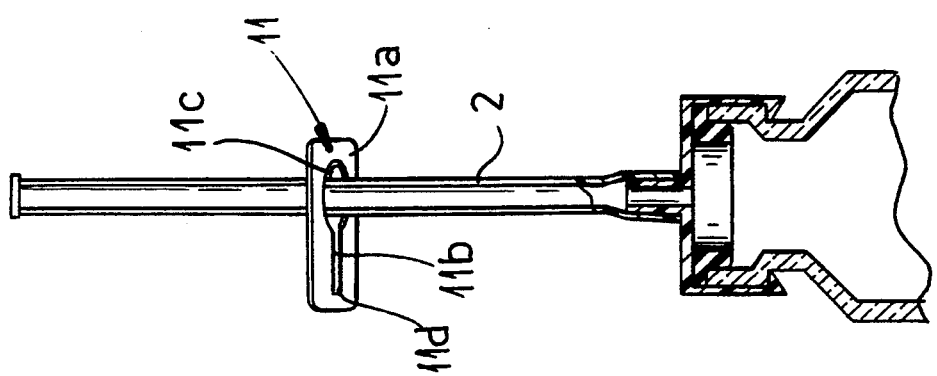

FIG. 5 shows the tube fitted with a clamp 11. This clamp may be used to temporarily shut off the flow of fluid through the tube.

The clamp may be a plastic or sheet metal plate 11a formed with a keyhole opening 11b whose large portion 11c accommodates the tube 2 without constriction, but whose narrow portion 11d can so constrict the tube as to prevent flow therethrough.

Figure 6:
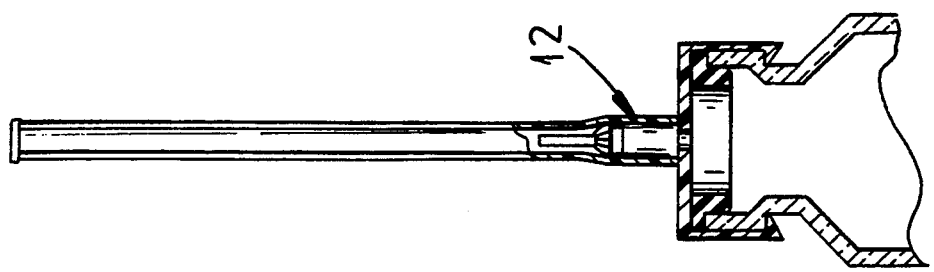

FIG. 6 shows the tube fitted with a break-away connector 12. This connector prevents the drug from reaching the seal of the tube. Drug in the seal may accidentally be thrown away with a piece of tube that is discarded in the sterile docking procedure, thus losing part of the dose. Also, drug in the seal may be burned during sterile docking, possibly leading to toxic degradation products. Therefore, it is generally desirable that the drug cannot reach the seal of the tube. For that purpose, a break-away connector can be provided in the tube.

Figure 7:
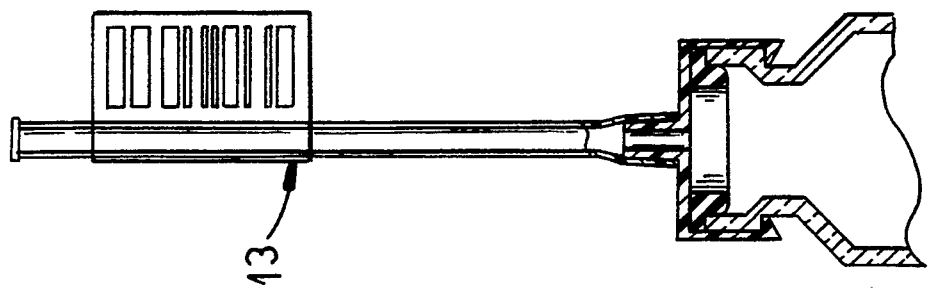
FIGS. 4 to 7 are sectional views like that of FIG. 1 showing further embodiments of this invention.

FIG. 7 shows the closure assembly according to the present invention in which the tube is fitted with a flag label 13 for identification. For identification purposes, the tube may also be fitted with numbers. The piece of tube containing such identification means can, after reconstitution, be left on the tube of the container or syringe that is filled with the drug solution thus allowing for positive identification.

In FIGS. 8A–8D, the method of reconstituting a drug in an IV solution in a flexible container is illustrated.

Figure 8D:
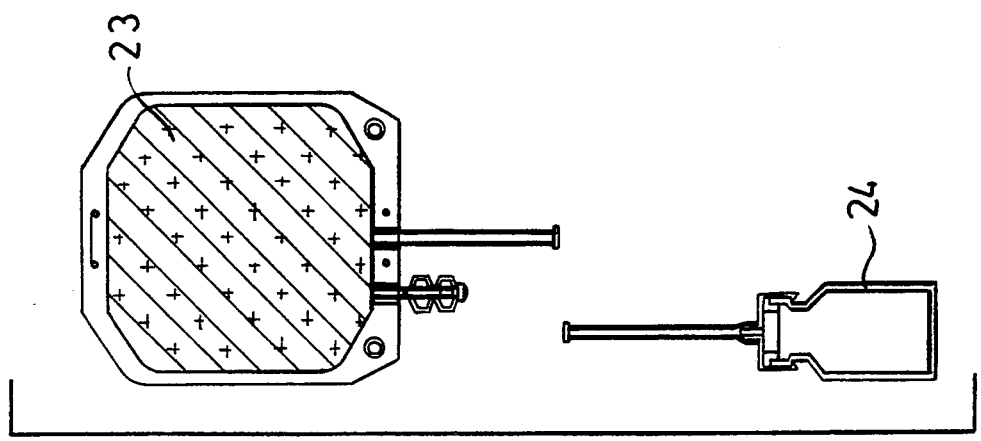
FIGS. 8A to 8D are largely schematic views illustrating the method of reconstituting a drug in a solution according to the present invention.
Figure 8C:
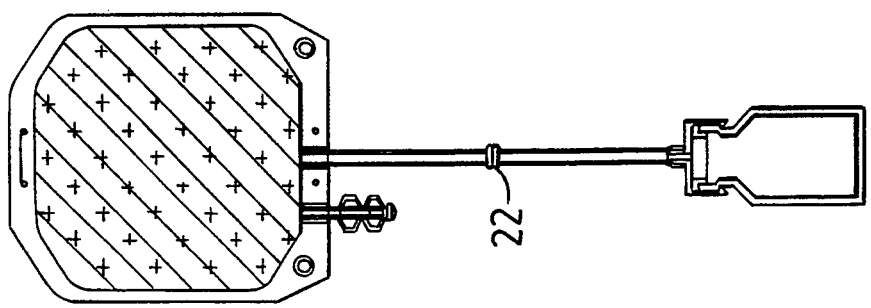
Figure 8B:
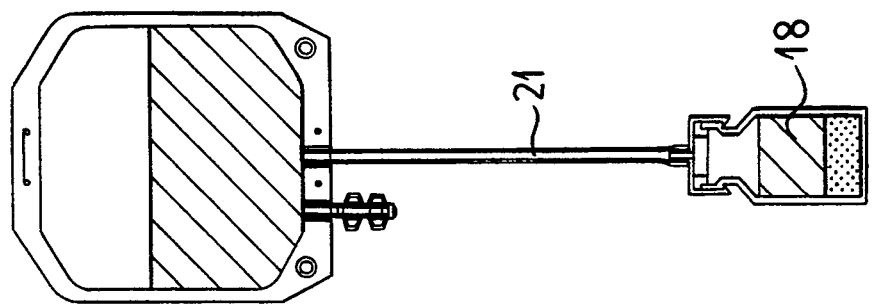
Figure 8A:
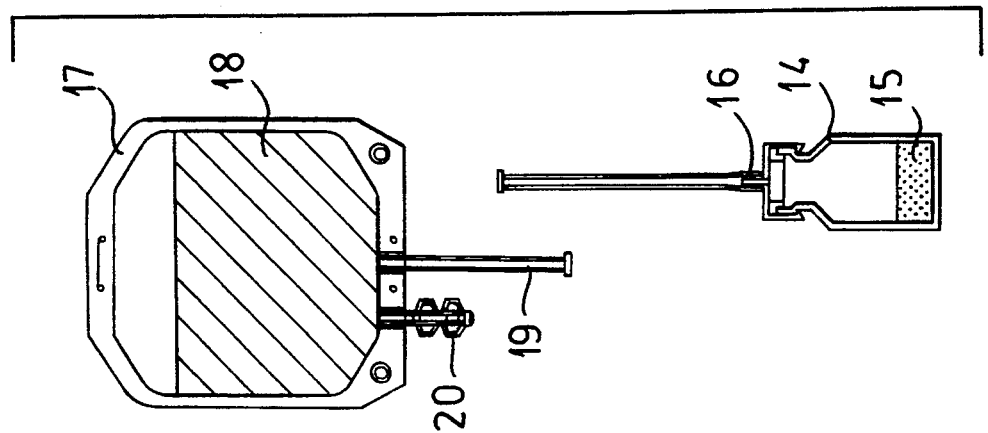

FIG. 8A shows a drug vial 14 with a medicament 15 that is fitted with a closure 16 according to the present invention. The vial is a standard rigid container made of e.g. glass or polyethylene and with sizes preferably according to ISO. In principle, any drug that is compatible with the material of the closure and the material of the container can be packaged in this vial. The sealable tube is long enough to allow for sterile docking. Usually, the length of this tube will be approx. 20 cm.

Also, the flexible IV container 17 with the IV solution 18 is fitted with a sealable tube 19 for sterile docking. The container is equipped with a butterfly port 20 for the administration of the solution to the patient.

As seen in FIG. 8B, the method of this invention comprises joining the sealed tube of this drug vial with a sealed tube of another component such as a flexible container (illustrated) with an intravenous solution or a syringe in a sterile docking unit as described in the above-mentioned patents. The sealable tubes are put in the apparatus for sterile docking where they are docked and joined together at 21. Thereby, open communication is achieved between the (sterile) insides of both tubes and thus between both components.

If the component is a flexible container fitted with a closed, sealable tube, a drug solution in said IV container can be prepared. If the drug is already dissolved, it can be mixed with the infusion solution immediately after sterile docking. If the drug is in the form of a powder, it must first be dissolved. For that purpose, after sterile docking fluid 18 is introduced into the drug vial by squeezing the flexible container. Concomitantly, air or gas is forced from the drug vial into the IV container. The drug can now be dissolved. When the drug is dissolved, it can be removed from the drug container by squeezing the flexible IV container and introducing some air or gas in the vial again. The drug solution will be expelled from the drug container and will be introduced into the flexible container.

As illustrated in FIG. 8C, the tube connecting the drug vial and the IV container can be sealed at 22 after the drug solution has been introduced into the flexible container. The drug vial is now empty.

There are several methods for sealing such as heat sealing or RF-welding. An apparatus for sealing tubes is marketed in the U.S. by the Sebra company. Several patents describe these sealing techniques such as U.S. Pat. Nos. 4,013,860, 4,186,292 and 4,390,832.

As illustrated in FIG. 8D, the seal can be cut, thus leaving an empty drug vial 24 with a sealed tube and a reconstituted IV drug solution in a flexible container 23 with a sealed tube.

After thorough mixing, this fluid can be administered to the patient.

If the tube on the drug vial is connected to a syringe with a closed sealable tube, the drug can be introduced into the syringe. Such a syringe is disclosed in copending U.S. patent application Ser. No. 07/719,728.

If the drug is already in a dissolved form it can be taken from the vial directly. If it is in a powdered form, the syringe must first be filled with a diluent from a flexible container with a closed sealable tube. Subsequently, after sterile docking, the diluent can be introduced into the drug vial, the drug dissolved in the diluent and finally the drug solution transferred from the vial into the syringe. Subsequently, the tube can be sealed and the seal can be cut, leaving a drug vial with a sealed tube and a syringe with a volume of drug solution and a sealed tube. From the syringe, the drug solution can be administered to the patient or can be further diluted in an IV solution.

Figure 9:
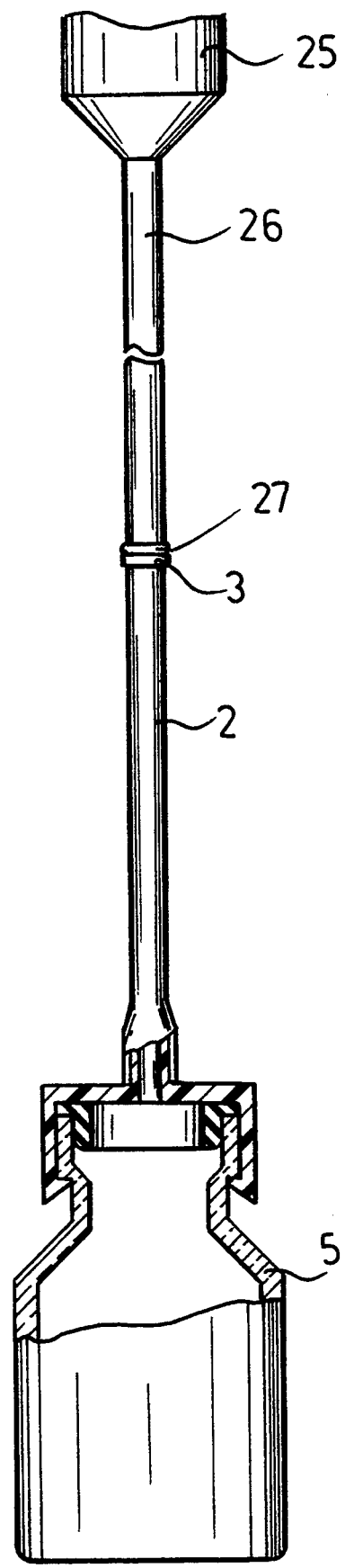
FIG. 9 is a fragmentary sectional view showing the vial connected to a syringe in the stage just before separation in sterile docking.

In FIG. 9, we have shown a syringe 25 connected by its tube 26 to the tube 2 of the vial 5 of FIG. 3 by the sterile docking procedure described, the seals 27 and 3 being formed between the tube 26 and the tube 2, respectively and prior to the severing of the sterile docking connection between these seals.

This closure assembly and the method for reconstituting or diluting a drug in an essentially closed system employing the technique of sterile docking offers many advantages over the state-of-the-art technique employing a needle to introduce a fluid and withdraw a drug solution from a drug vial in an open system.

The main advantage of the closure assembly according to the present invention is that it allows for transferring a sterile drug and a sterile fluid between a drug vial and an IV container in a closed system. Use of such a closed system will prevent foreign material from accidentally entering the drug solution and it will prevent the escape of the drug to the environment. Furthermore, the generally tiresome and dangerous procedure of working with needles is avoided. The method of this invention is fast, convenient and safe.

Prevention of foreign material entering the drug solution has far-reaching consequences. Prevention of microbiological contamination will increase the safety of reconstituted IV solutions and may reduce hospital-acquired infection in patients. Furthermore, it will increase the shelf-life of many reconstituted products, thus making recycling of unused doses possible. Finally, use of sterile docking allows for reconstitution outside LAF-cabinets and does not require the use of demanding aseptic techniques of the operator.

The use of sterile docking also prevents spillage of drug solution into the environment. This increases the safety of working with hazardous substances like cytostatic drugs by reducing the chances of inadvertent exposure to these drugs due to aerosols, needle drips, leaking closures and the like. Also, the waste that is generated during reconstitution according to the present invention is sealed and thus poses no immediate hazard to the operator and the environment.

Generally, the replacement of needles by a fluid path consisting of two tubes in open fluid communication, offers a number of advantages. In the first place, needle pricks are prevented. In the second place, the flexible container cannot be punctured accidentally. In the third place, use of tubes is far more convenient as needles require considerable force during injection and withdrawal of fluids. In the fourth place, as no rubber membrane membrane needs to be punctured, no coring or laceration resulting in particles can take place.

I claim:

1. A closure assembly for a drug vial comprising a body that on one side can fit hermetically on a mouth of a drug vial, and a flexible elongated radiofrequency and heat weldable tube attached at one end of said tube to an opposite side of said body, an inside of said tube being in communication with an inside of said drug vial after mounting of said closure assembly on said vial an opposite end of said tube remote from said vial being sealed hermetically.

2. The closure assembly defined in claim 1, further comprising an adaptor mounted on said body that can receive said drug vial with a tight grip, thus producing a hermetically closed transition between said drug vial and said body of said closure.

3. The closure assembly defined in claim 1 wherein said tube contains a filter spaced by a length of said tube from said vial for the removal of particulate matter.

4. The closure assembly defined in claim 1, further comprising a clamp on said tube spaced from said vial for temporarily shutting off the flow of fluid.

5. The closure assembly defined in claim 1, further comprising a break-away connector along said tube.

6. The closure assembly defined in claim 1 further comprising a means for identification on said tube.

7. A medical product consisting of a drug packaged in a vial, said vial being fitted with a closure having a body with a closed elongated flexible radiofrequency and heat weldable tube, an inside of said tube being in communication with an inside of said drug vial.

8. The medical product defined in claim 7 wherein said closure is tightly and hermetically secured to said vial be means of an external cap.

9. The medical product defined in claim 7 wherein said body of said closure is provided with an integrated adaptor that tightly and hermetically secures said body of said closure to the mouth of said drug vial.

10. The medical product defined in claim 7 wherein said product is fitted with a tamper evidence between the closure and the vial.

11. The medical product defined in claim 7 wherein said tube is fitted with a filter for the removal of particulate matter.

12. The medical product defined in claim 7 wherein said tube is fitted with a clamp to temporarily shut off the flow of fluid therethrough.

13. The medical product defined in claim 7 wherein said tube is fitted with a break-away connector.

14. The medical product defined in claim 7 wherein said tube is fitted with a means for identification.

15. A method for preparing a sterile medical solution, comprising the steps of:
making open fluid communication between a drug in a drug vial fitted with a closure with a closed elongated flexible radiofrequency and heat weldable tube an inside of which is in communication with an inside of said vial, and a second component also fitted with a closed elongated flexible radiofrequency and heat weldable tube by sterile docking; and
transferring material between said drug vial and said second component.

16. The method defined in claim 15, further comprising the step of radiofrequency or heat welding said tube between said drug vial and said second component after introduction of said drug solution in said second component.

17. The method defined in claim 16, further comprising the step of cutting said radiofrequency or heat weld between said second component and said vial into two parts.

18. The method defined in claim 15 wherein said second component is a flexible IV container containing an IV solution and said drug is mixed with said solution.

19. The method defined in claim 15 wherein said second component is a syringe.

20. An intermediate assembly for use in the intravenous administration of a medicament, comprising:
an IV bag containing a liquid vehicle for a medicament and formed with an elongated flexible radiofrequency and heat weldable tube having an end remote from said bag; and
a vial containing said medicament and provided with a mouth and an elongated flexible radiofrequency and heat weldable tube extending from said mouth and formed with an end remote from said mouth sealed hermetically to the end of said tube formed on said bag whereby connection is established between said vial and said bag.

* * * * *